(12) United States Patent
Kuramochi

(10) Patent No.: US 11,234,871 B2
(45) Date of Patent: Feb. 1, 2022

(54) ABSORBENT ARTICLE

(71) Applicant: DAIO PAPER CORPORATION, Ehime (JP)

(72) Inventor: Mihoko Kuramochi, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 540 days.

(21) Appl. No.: 16/319,616

(22) PCT Filed: Jul. 20, 2017

(86) PCT No.: PCT/JP2017/026290
§ 371 (c)(1),
(2) Date: Jan. 22, 2019

(87) PCT Pub. No.: WO2018/037783
PCT Pub. Date: Mar. 1, 2018

(65) Prior Publication Data
US 2020/0121517 A1    Apr. 23, 2020

(30) Foreign Application Priority Data
Aug. 25, 2016   (JP) .............................. JP2016-165033

(51) Int. Cl.
*A61F 13/47* (2006.01)
*A61F 13/472* (2006.01)
*A61F 13/51* (2006.01)

(52) U.S. Cl.
CPC .... *A61F 13/4702* (2013.01); *A61F 13/47245* (2013.01); *A61F 2013/51078* (2013.01)

(58) Field of Classification Search
CPC .... A61F 13/47; A61F 13/4702; A61F 13/472; A61F 13/47236; A61F 13/47245;
(Continued)

(56) References Cited

U.S. PATENT DOCUMENTS

2004/0243087 A1   12/2004   Kinoshita et al.
2014/0288520 A1    9/2014   Kuramochi
(Continued)

FOREIGN PATENT DOCUMENTS

JP           3871611      1/2007
JP       2011-172658      9/2011
(Continued)

OTHER PUBLICATIONS

International Search Report for PCT/JP2017/026290 dated Sep. 5, 2017.
(Continued)

*Primary Examiner* — Catharine L Anderson
(74) *Attorney, Agent, or Firm* — IPUSA, PLLC

(57) ABSTRACT

An absorbent article (1) includes a hip hold portion (H) and a main body (8) including a liquid-pervious topsheet (3), a liquid-impervious backsheet (2), and an absorbent member (4) arranged between the topsheet and the backsheet. The main body has a shape with a prescribed length in the front-back direction and a prescribed width in the direction orthogonal to the front-back direction. The hip hold portion includes a side region (10) protruding from a backward side portion of the main body, and the side region includes a first protrusion (41) including a portion having a greatest width from a front-back direction centerline of the main body, a first recess (51) that is in front of and adjacent to the first protrusion, and a second protrusion (42) that is in front of and adjacent to the first recess. The outline of the first recess includes a curved line, and a rigid area (70) including one or more rigid portions (60) with enhanced rigidity is provided on a first imaginary line passing through a bottom point of the first recess and a center of a circle of curvature of a curve at the bottom point of the first recess.

5 Claims, 7 Drawing Sheets

(58) Field of Classification Search
CPC .... A61F 2013/4706; A61F 2013/51078; A61F 2013/5108; A61F 2013/51083; A61F 2013/51085
See application file for complete search history.

(56) References Cited

U.S. PATENT DOCUMENTS

2017/0135864 A1\* 5/2017 Nomoto ................ A61F 13/513
2019/0290506 A1\* 9/2019 Kuramochi ........... A61F 13/513

FOREIGN PATENT DOCUMENTS

| JP | 5082007 | 11/2012 |
| JP | 2014-144140 | 8/2014 |
| JP | 2014-223216 | 12/2014 |
| JP | 2016-104095 | 6/2016 |
| JP | 2016-119988 | 7/2016 |
| JP | 2016-119989 | 7/2016 |

OTHER PUBLICATIONS

Extended European search report for European Patent Application No. 17843270.4 dated Jul. 22, 2019.

\* cited by examiner (a)

(b)

ABSORBENT ARTICLE

TECHNICAL FIELD

The present invention relates to an absorbent article.

BACKGROUND ART

Conventionally, absorbent articles such as panty liners, sanitary napkins, incontinence pads, and the like have an absorbent member arranged between a liquid-pervious topsheet and a liquid-impervious backsheet. Further, in recent years, there are absorbent articles that have an extended portion having a large length and a large width extending from the backward side portions to the back end portion of the absorbent article for preventing body fluids from leaking backward and/or obliquely backward from the absorbent article.

For example, Patent Document 1 describes an absorbent article provided with a rear flap comprising a liquid-impervious sheet and a nonwoven fabric layered on a skin contact surface side of the liquid-impervious sheet. The rigidity of the rear flap is enhanced by performing a heat embossing process on the layered structure having the nonwoven fabric layered on the liquid impeable sheet to form an uneven pattern.

Also, Patent Document 2 describes an absorbent article having a flap portion that is arranged behind a wing portion and projects outward in the width direction from a main body portion. The flap portion includes a constricted portion having a width direction dimension that is shorter than the width direction dimensions of other regions of the flap portion in front of and behind the constricted portion, a first flap portion located in front of the constricted portion and protruding outward in the width direction from the constricted portion, and a second flap portion located behind the constricted portion and protruding outward in the width direction from the constricted portion. The flap portion further includes a recessed portion that is recessed in the thickness direction of the flap portion and extends rearward from the inner side in the width direction toward the outer side in the width direction to reach the constricted portion.

PRIOR ART DOCUMENTS

Patent Documents

Patent Document 1: Japanese Patent No. 3871611
Patent Document 2: Japanese Patent No. 5082007

SUMMARY OF THE INVENTION

Problem to be Solved by the Invention

However, because a heat embossing process is performed on the entire rear flap portion of the absorbent article of Patent Document 1, the flap portion becomes rigid to thereby compromise wearing comfort.

In the absorbent article of Patent Document 2, the flap portion is configured to be folded along the recessed portion. As such, depending on the wearing state, the folded portion may form large wrinkles that come into contact with the skin to cause discomfort.

In consideration of the above problems of the related art, it is an object of the present invention to provide an absorbent article that can prevent the formation of wrinkles at a hip hold portion and that can disperse wrinkles even when they are formed to thereby improve wearing comfort.

Means for Solving the Problem

According to a first embodiment of the present invention, an absorbent article is provided that includes a main body including a liquid-pervious topsheet, a liquid-impervious backsheet, and an adsorbent member arranged between the topsheet and the backsheet; and a hip hold portion. The main body has a shape with a prescribed length in a front-back direction and a prescribed width in a direction orthogonal to the front-back direction. The hip hold portion includes a side region protruding from a backward side portion of the main body, and the side region includes a first protrusion including a portion with a greatest width from a front-back direction centerline, a first recess that is in front of and adjacent to the first protrusion, and a second protrusion that is in front of and adjacent to the first recess. An outline of the first recess includes a curved line, and a rigid area including one or more rigid portions with enhanced rigidity is provided on a first imaginary line passing through a bottom point of the first recess and a center of a circle of curvature of a curve at the bottom point of the first recess.

According to the above-described first embodiment of the present invention, the side region of the hip hold portion includes a first protrusion including a portion with a greatest width from a front-back direction centerline, a first recess that is in front of and adjacent to the first protrusion, and a second protrusion that is in front of and adjacent to the first recess. As such, when the absorbent article is attached so that the hip hold portion comes into contact with the buttocks, because the first recess is provided between the first protrusion and the second protrusion, the first protrusion and the second protrusion may be deformed independently without being influenced by each other. In this way, the hip hold portion may be deformed along the curved shape (roundness) of the buttocks, and body fit of the hip hold portion may be improved.

However, depending on the state of contact between the hip hold portion and the buttocks, the body weight applied to the buttocks, and the like, a relatively large load may be applied to the outer peripheral region of the hip hold portion due to the movement of the body. In such a case, because stress tends to concentrate in a recess, wrinkles tend to form in the vicinity of the recess of the hip hold portion, particularly in the vicinity of the first recess that is in front of and adjacent to the first protrusion having the greatest width.

In this respect, according to the present embodiment, a rigid area including one or more rigid portions with enhanced rigidity is provided on a first imaginary line passing through a bottom point of the first recess and the center of the circle of curvature of the curve at the bottom point of the first recess to enhance the rigidity in the vicinity of the first recess. In this way, even when stress becomes concentrated in the vicinity of bottom point of the first recess, the formation or wrinkles may be prevented. Further, even when a force that causes the formation of wrinkles is applied, the wrinkles may be dispersed toward the side regions of the rigid area such that the formation of large wrinkles may be prevented. In this way, discomfort caused by the formation of large wrinkles that come into contact with the skin may be substantially eliminated.

According to a second embodiment of the present invention, the rigid portion or the rigid area has an elongated shape, and a longitudinal direction of the elongated shape is substantially parallel to a second imaginary line that is orthogonal to the first imaginary line. In this way, the rigid portion or the rigid area may extend across a wider range in the direction of the second imaginary line that is orthogonal to the first imaginary line. As such, even when a wrinkling force is applied, the formation of wrinkles may be prevented across a wider range in the direction that is orthogonal to the direction in which wrinkles are likely to form. Also, even when wrinkles are famed, the wrinkle dispersing effect may be improved.

According to a third embodiment of the present invention, the rigid portion is an embossed portion.

According to the above-described third embodiment, by arranging the rigid portion to be an embossed portion, the rigidity of the rigid portion may be improved. Also, because the rigid portion is a compressed portion, it is less likely to cause discomfort even when the hip hold portion is pressed against the skin, and in this way, an absorbent article with excellent wearing comfort may be provided.

According to a fourth embodiment of the present invention, a plurality of embossed dots are provided at a peripheral portion of the side region, and an area of the rigid portion in the rigid area is greater than or equal to 10 times and less than or equal to 25 times the area of one of the embossed dots.

According to the above-described fourth embodiment, by providing a plurality of embossed dots at the peripheral portion of the side region, and arranging the area of the rigid portion in the rigid area to be greater than or equal to 10 times and less than or equal to 25 times the area of one of the embossed dots, the hip hold portion as a whole may be provided with an appropriate rigidity that can achieve a good balance between wrinkle prevention and wearing comfort.

According to a fifth embodiment of the present invention, a plurality of the rigid portions are radially arranged in the rigid area to form a flower shape. In this way, the area of each of the plurality of rigid portions may be reduced while maintaining their rigidity enhancing effects. Thus, discomfort caused by the rigid portion coming into contact with the skin may be minimized or substantially eliminated. Also, the absorbent article may be improved aesthetically as well.

According to a sixth embodiment of the present invention, a plurality of the rigid areas are arranged along the first imaginary line, and an area of a rigid area closer to the centerline is arranged to be smaller than an area of a rigid area farther away from the centerline.

According to the above-described sixth embodiment, by providing a plurality of rigid areas and arranging the area of a rigid area closer to the centerline to be smaller than the area of a rigid area farther away from the centerline, a rigid area located at a position that is more likely to come into contact with the skin may be arranged to be smaller. In this way, discomfort caused by a rigidity-enhanced portion coming into contact with the skin may be reduced while maintaining wrinkle preventing effects at the recess.

Advantageous Effect of the Invention

According to an aspect of the present invention, an absorbent article that can prevent the formation of wrinkles at a hip hold portion and that can disperse wrinkles even when they are formed to thereby achieve excellent wearing comfort may be provided.

EMBODIMENTS FOR IMPLEMENTING THE INVENTION

In the following, embodiments of the present invention will be described with reference to the accompanying drawings.

Figure 1:
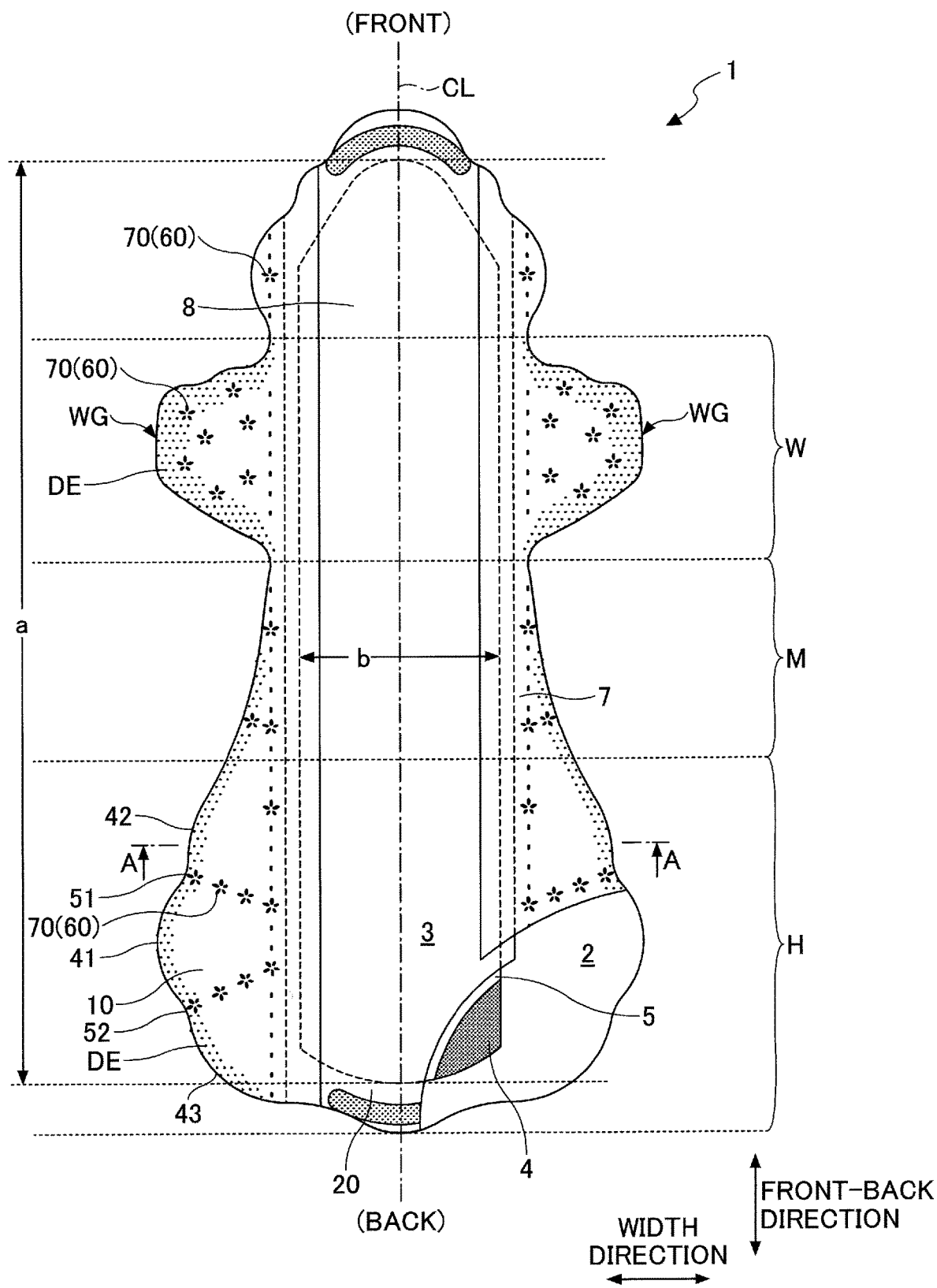
FIG. 1 shows a partially cut view of an absorbent article according to an embodiment of the present invention.
Figure 2:
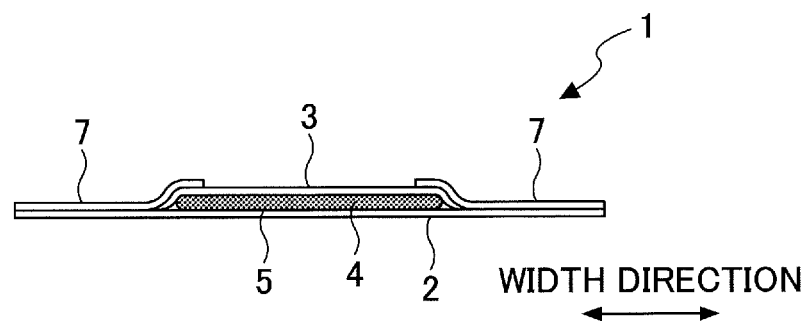
FIG. 2 shows a cross-sectional view across line A-A of the absorbent article according to an embodiment of the present invention.

As shown in FIGS. 1 and 2, the absorbent article 1 includes a main body (absorbent article main body) 8 including a liquid-impervious backsheet 2, a liquid-pervious topsheet 3, and an absorbent member 4 arranged between the two sheets 2 and 3. The absorbent member 4 may be wrapped in a wrapping sheet 5, which may be made of crepe paper, nonwoven fabric, or the like, to maintain the shape of the absorbent member 4. As shown in FIG. 1, the absorbent article 1 further includes a hip hold portion H, a wing portion W having a wing WG, and an intermediate portion M arranged between the hip hold portion H and the wing portion W. The intermediate portion M may be a region extending from the rear end of the wing WG to the front end of a second protrusion 42.

The absorbent article 1 may be used by attaching it to underwear so that the wing portion W side faces the front direction and the hip hold portion H side faces the backward direction. As shown in FIG. 1, the main body 8, as a whole, has an elongated shape having a prescribed length "a" in the front-back direction and has a certain width "b" in a direction orthogonal to the front-back direction. The absorbent article 1 is substantially line-symmetrical with respect to a centerline CL extending in the front-back direction.

At the front and rear edge portions of the absorbent member 4, the outer edges of the backsheet 2 and the outer edges of the topsheet 3 are adhered to each other by an adhesive such as a hot melt or adhesion means such as a heat seal or an ultrasonic seal, for example. Also, a side nonwoven fabric 7 extending in the front-back direction (longitudinal direction) is arranged on each lateral side portion of the topsheet 3. The side nonwoven fabric 7 partially protrudes from the lateral side of the main body 8 and is layered on the backsheet 2 that also protrudes from the lateral side of the main body 8, and the protruding portions are adhered to each other by an adhesive such as a hot melt or adhesive means such as a heat seal or an ultrasonic seal, for example. In this way, a side region 10 of the hip hold portion H and the wing WG are formed.

The backsheet 2 may be made of a sheet material having at least water-blocking properties. For example, an olefin-based resin sheet such as a polyethylene sheet or a polypropylene sheet may be used. Also, a laminated nonwoven fabric formed by laminating a nonwoven fabric on a polyethylene sheet or the like, or a nonwoven fabric laminated sheet having a waterproof film interposed therein to secure substantial liquid impermeability may be used. Further, a moisture-permeable sheet is preferably used in order to prevent stuffiness. An example of such a water-impermeable/moisture-permeable sheet material includes a macroporous sheet obtained by forming a sheet through melt-kneading an inorganic filler in an olefin-based resin such as polyethylene or polypropylene and stretching the sheet in a uniaxial direction or biaxial directions.

The topsheet 3 is a liquid-pervious sheet that allows body fluids such as menstrual blood, vermilion, urine, and the like to promptly permeate the liquid-pervious sheet. Examples of suitable materials that may be used as the topsheet 3 include a perforated or nonporous nonwoven fabric, a porous plastic sheet, and the like. Examples of material fibers constituting the nonwoven fabric include olefin fibers such as polyethylene and polypropylene, synthetic fibers such as polyester and polyamide, recycled fibers such as rayon and cupra, mixed fibers thereof, and natural fibers such as cotton. Note that these fibers may be used alone or in any combination. Example processing methods for faulting the nonwoven fabric include a spun lace method, a spun bond method, a thermal bond method, a melt blown method, a needle punch method, and the like. Among these processing methods, the spun lace method is preferable in terms of flexibility, the spun bond method is preferable in terms of producing a nonwoven fabric rich in draping properties, and the thermal bonding method is preferable in terms of producing a bulky and soft nonwoven fabric. Also, multi-component fibers such as sheath-core fibers having fiber with a high melting point as a core and fiber with a low melting point as a sheath, side-by-side fibers, split fibers, and the like may be used, for example.

The absorbent member 4 interposed between the backsheet 2 and the topsheet 3 is not particularly limited as long as it is a material capable of absorbing and retaining body fluids, but for example, the absorbent member preferably includes cotton-like pulp and water-absorbent polymer. Examples of the water-absorbing polymer that may be used include superabsorbent polymer (SAP), superabsorbent fiber (SAF), and combinations thereof. Examples of the pulp include cellulose fibers such as chemical pulp obtained from wood, dissolving pulp, and the like, and artificial cellulose fibers such as rayon, acetate, and the like. Note that hardwood materials, softwood materials, and the like may be used as the raw material for chemical pulp, but softwood materials are preferably used in view of their long fiber length and the like.

Also, a synthetic fiber may be mixed into the absorbent member 4. Examples of the synthetic fiber that may be used include polyolefins such as polyethylene and polypropylene, polyesters such as polyethylene terephthalate, polybutylene terephthalate and the like, polyamides such as nylon, and copolymers thereof. Note that a combination of two or more of these materials may also be used. Also, multi-component fibers such as sheath-core fibers having fiber with a high melting point as a core and fiber with a low melting point as a sheath, side-by-side fibers, split fibers, and the like may be used, for example. Also, hydrophobic fiber that has been surface-treated with a hydrophilizing agent to exhibit affinity to body fluids may be used, for example.

Note that the thickness of the absorbent member 4 is within the range from about 0.5 mm to about 25 mm. The absorbent member 4 does not have to have a uniform thickness across its entire surface. For example, the absorbent member 4 may have a structure with a bulging portion corresponding to a body fluid discharge site. Further, the absorbent member 4 is preferably manufactured by a stacking process or an air laid process.

Example materials that may be used as the side nonwoven fabric 7 include a hydrophobically treated nonwoven fabric and a hydrophilically treated nonwoven fabric. For example, in the case of enhancing the effect of preventing permeation of menstrual blood or vaginal discharge or improving tactile feeling, a water-repellent treated nonwoven fabric coated with a silicon-based, a paraffin-based, an alkyl chromic chloride-based water repellent or the like may be used. Also, for example, in the case of enhancing absorbability of menstrual blood or the like at the hip hold portion H, a hydrophilically treated nonwoven fabric may be used as the material of the nonwoven fabric. Note that air-through nonwoven fabrics are a suitable type of nonwoven fabric that may be used because they are soft and not susceptible to creasing and wrinkling.

In the present embodiment, the absorbent article 1 includes a main body 8 including a liquid-pervious topsheet 3, a liquid-impervious backsheet 2, and an absorbent member 4 arranged between the topsheet 3 and the backsheet 2; and a hip hold portion H.

Figure 10:
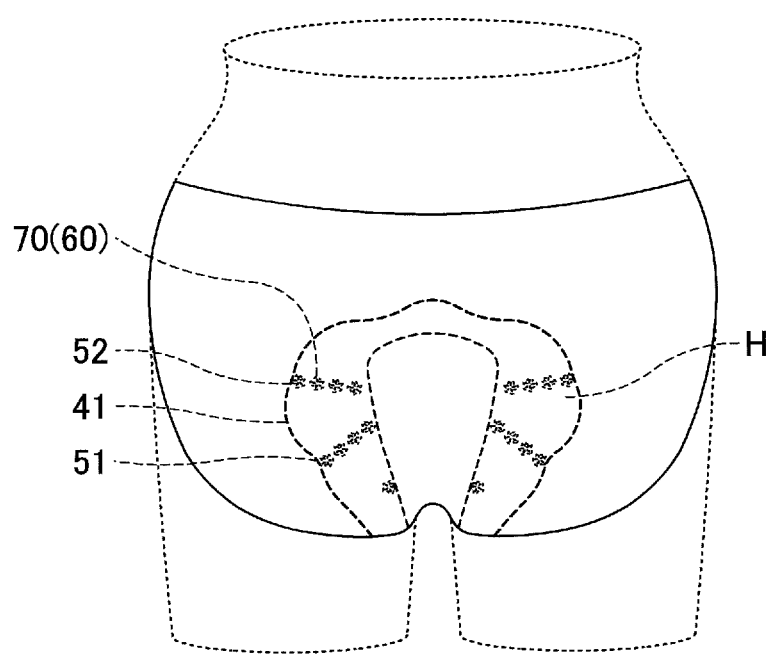
FIG. 10 is a model diagram showing an attached state of an absorbent article according to an embodiment of the present invention.

The hip hold portion H is an area expanded portion formed by increasing the length and width of the portion extending from the rearward side portions and the rear end portion of the absorbent article 1. By fixing the hip hold portion H to the buttock inner surface side of underwear as shown in FIG. 10, the hip hold portion H serves the function of preventing body fluids from leaking rearward and/or diagonally rearward of the absorbent article 1. As shown in FIG. 1, the hip hold portion H includes a flap-like portion having the side nonwoven fabric 7 laminated on the backsheet 2 and extending from the rearward side portions to the rear end portion of the main body 8 of the absorbent article 1.

The hip hold portion H includes a side region 10 protruding from the backward side portion of the main body 8 and a back region 20 protruding from the back end portion of the main body 8. The side region 10 of the hip hold portion H mainly includes a region formed by bonding together the backsheet 2 and the side nonwoven fabric 7, and the back region 20 mainly includes a region formed by bonding together the backsheet 2 and the topsheet 3.

Note that the side region 10 and the back region 20 of the hip hold portion H preferably do not have the absorbent member 4 arranged therein so that these regions would be thinner than the main body 8. In this way, more flexible movement may be enabled in these regions as compared with the main body 8. Note, however, that in some embodiments, an absorbent member that is configured to be thinner than the absorbent member 4 used in the main body 8 may be arranged between the backsheet 2 and the side nonwoven fabric 7 of the side region 10 of the hip hold portion H, for example.

The hip hold portion H, when attached to underwear, corresponds to a portion extending from a position at the rear end of the crotch portion of the underwear to the rear end of the absorbent article 1. In the example shown in FIG. 1, the hip hold portion H may be a portion extending from the position of the front end of the second protrusion 42 to the rear end of the absorbent article 1. For example, the length in the front-back direction of the hip hold portion H is preferably greater than or equal to 50 mm and less than or equal to 200 mm, and more preferably greater than or equal to 80 mm and less than or equal to 180 mm. Also, the total length of the absorbent article 1 may be greater than or equal to 200 mm and less than or equal to 450 mm, and the length in the front-back direction of the hip hold portion H is preferably greater than or equal to 10% and less than or equal to 50% of the total length of the absorbent article 1. Note that the hip hold portion H includes a portion having the greatest width of the absorbent article 1, the width at this portion preferably being greater than or equal to 120 mm and less than or equal to 230 mm. Further, the outer periphery (outline) of the hip hold portion H is preferably arranged to be uneven. For example, in FIG. 1, the side region 10 includes a first protrusion 41 including a portion having the greatest width from a front-back direction centerline CL of the main body 8, a first recess 51 that is in front of and adjacent to the first protrusion 41, and a second protrusion 42 that is in front of and adjacent to the first recess 51.

In the following, the effects of forming the unevenness along the outer periphery of the hip hold portion H will be described.

The hip hold portion H is flat as a whole. When such a flat hip hold portion H is brought into contact with the buttocks, because the buttocks have a curved shape, distortion occurs particularly at the outer peripheral regions of the hip hold portion H due to the differences in shape between flat hip hold portion H and the curved shape of the buttocks, and as a result, wrinkles may be formed. Although the size and the number of wrinkles that are formed depend on the area of the entire hip hold portion H and the curvature of the buttocks, in the case where the protrusions and recesses as described above are not formed along the outer periphery of the hip hold portion H, a plurality of large wrinkles may be formed at a plurality of locations in the outer peripheral regions of the hip hold portion H. Such large wrinkles cause discomfort to the wearer when the wrinkles come into contact with the skin of the buttocks. Such discomfort may be particularly exacerbated when sitting in a chair for a long time or lying on the back while sleeping at night, for example, because a part of the body weight is applied to the buttocks. Also, wrinkles may become even larger when the body weight applied to the buttocks and/or the state of contact between the buttocks and the hip hold portion H changes due to a change of posture during sleep or while sitting, for example. Further, in the case of lying on the back or lying on the side while sleeping at night, for example, body fluids may leak through gaps foamed by such wrinkles.

In this respect, according to the present embodiment, the outer shape of the hip hold portion H is configured to have a recess between two protrusions. With such a configuration, for example, even when a force that causes wrinkling acts on the first protrusion 41, because the recess 51 is provided between the first protrusion 41 and the second protrusion 42, propagation of the force generated at the first protrusion 41 into the second protrusion 42 may be prevented, and as such, the force generated at the first protrusion 41 may be confined within the area of the first protrusion 41. The same applies to the case where a force that causes wrinkling acts on the second protrusion 42. In this way, the first protrusion 41 and the second protrusion 42 may be prevented from exerting influences on each other and may be configured to deform independently. Also, even when wrinkles are formed, the wrinkles may be prevented from becoming larger.

Thus, when attaching the absorbent article 1, the hip hold portion H may deform along the curved surface of the buttocks when the hip hold portion H comes into contact with the curved surface of the buttocks. In this way, improved fit of the hip hold portion H with respect to the buttocks may be achieved.

Note that in the illustrated embodiment, the side region 10 of the hip hold portion H is configured to have the first protrusion 41, the first recess 51, and the second protrusion 42 arranged at its outer periphery. However, the number of protrusions and recesses and/or the shape of the outer periphery are not limited to the illustrated example. For example, the side region 10 of the hip hold unit H may be configured to have two to five protrusions and one to five recesses arranged at its outer periphery.

As described above, by arranging the outer periphery of the hip hold portion H to be uneven, body fit of the hip hold portion H may be improved. However, depending on the state of contact between the hip hold portion H and/or the manner in which the body weight is applied to the buttocks, a relatively large load may be applied to the outer peripheral region of the hip hold portion H are a result of a force being applied from the buttocks when the legs or buttocks are moved or a force being transmitted from the front portion including the intermediate portion M of the absorbent article 1, for example. In such case, wrinkles are easily formed at a recess where concentration of stress is likely to occur. Specifically, wrinkles are likely to occur at the first recess 51, which is arranged in front of and adjacent to the first protrusion 41 having the greatest width, particularly along the direction of a line passing a bottom point P of the first recess 51 and a center O of a circle of curvature of the curve at the bottom point P of the first recess 51.

Figure 3:
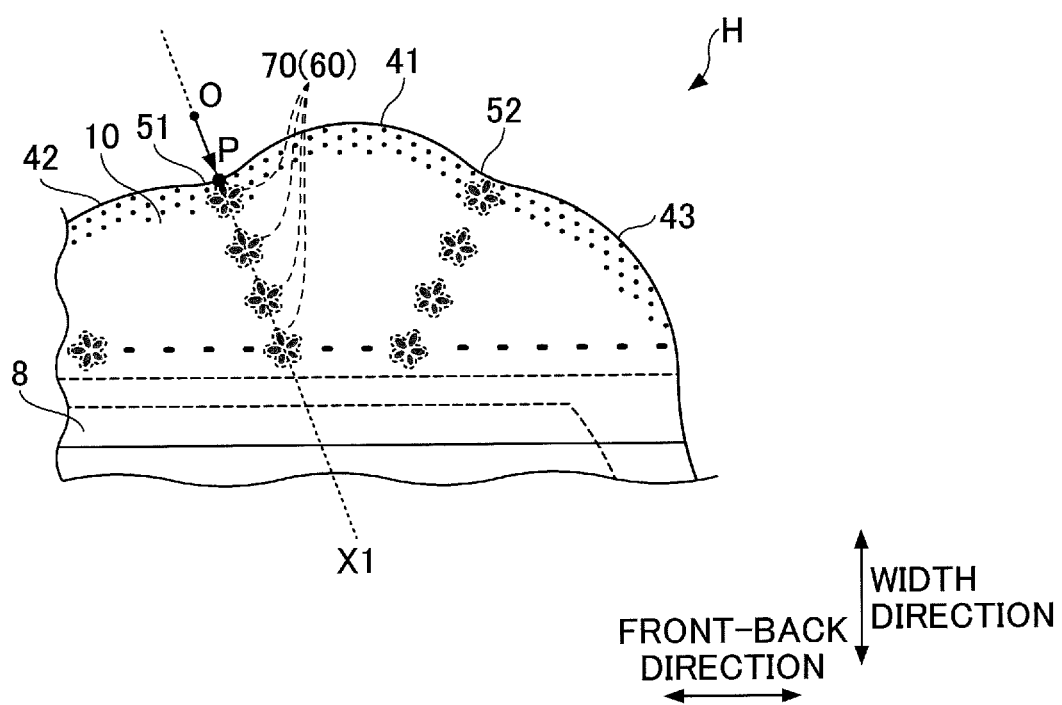
FIG. 3 shows a partial enlarged view of a hip hold portion according to an embodiment of the present invention.

In this respect, according to the present embodiment, as illustrated in FIGS. 1 to 3, the outline of the first recess 51 is arranged into a curved line, and a rigid areas 70 including one or more rigid portions 60 with enhanced rigidity is arranged on a first imaginary line X1 passing through the bottom point P of the first recess 51 and the center O. That is, a rigid area 70 is arranged on the first imaginary line X1 that passes through the bottom point P of the first recess 51 and the center O of a circle formed by an arc approximating the curved line passing through the bottom point P and points infinitesimally close to the bottom point P of the first recess 51.

In this way, the formation of wrinkles in the vicinity of the bottom point P of the first recess 51 may be prevented. Further, even when wrinkles are formed, the wrinkles can be dispersed around the rigid areas 70. For example, wrinkles may be dispersed toward the first protrusion 41 side and the second protrusion 42 side, resulting in smaller wrinkles. Note that because small wrinkles formed by such dispersion protrude at lower heights as compared with larger wrinkles, they are less likely to cause discomfort upon coming into contact with the skin. In this way, the wearing comfort of the absorbent article 1 may be improved.

Note that although the outline of the first recess 51 is a curved line in the illustrated example, a part of the outline of the first recess 51 may be a straight line, for example. Also, the slopes of tangential lines at the points of transition to the outlines of the protrusions at the front and back sides of the first recess 51 may be arranged to change abruptly, for example. The same also applies to recesses and protrusions other than the first recess 51.

Note that in the present description, the rigid portion 60 refers to a portion that has been subjected to processing to enhance rigidity. Although there is no particular limitation on the processing means for enhancing the rigidity, the rigid portion 60 is preferably a compressed portion famed by compression. For example, the rigid portion 60 may preferably be an embossed portion formed by a heat embossing process, an ultrasonic embossing process, or the like.

The rigid portion 60 may also be formed by applying a resin composition or the like to the portion and solidifying the resin composition or by stacking sheets to increase the thickness of the portion, for example. Such a thickened portion may be formed on the backsheet 2 or interposed between the backsheet 2 and the side nonwoven fabric 7, for example.

Further, in the present description, the rigid area 70 refers to an area (region) including one or more of the above-described rigid portions 60 and surrounding portions thereof. That is, the rigid area 70 includes the rigid portion 60 that has been subjected to processing as well as a portion that has not been directly subjected to processing but has enhanced rigidity in comparison to other portions of the side region 10 as a result of the processing performed on the rigid portion 60. For example, in the case where the rigid portion. 60 is formed by a compression process such as an embossing process, there may be portions surrounding the compressed portion that have altered thicknesses as a result of the compression process. Further, there may be portions that have altered rigidity as a result of influences (including influences of heat and the like) from the surrounding portions with the altered thicknesses.

Note that in the drawings, the rigid area 70 is indicated by a dotted line surrounding one or more rigid portions 60. The illustrated rigid area 70 is merely a conceptual example, and the shape and size of the rigid area 70 may vary depending on various factors such as the shape, size, and arrangement of the rigid portion 60, the method and conditions for processing the rigid portion 60, and the like.

Although the shape of the rigid portion 60 is not particularly limited, for example, the planar view shape of the rigid portion 60 may be a triangle; a quadrangle such as a trapezoid, a rhombus, or the like; some other polygon; a circle; an ellipse; an almond shape; a raindrop shape; a star shape; a heart shape; a diamond shape; a spade shape; a club shape; or the like. Note that FIG. 4 shows example shapes of the rigid portion 60.

Figure 4:
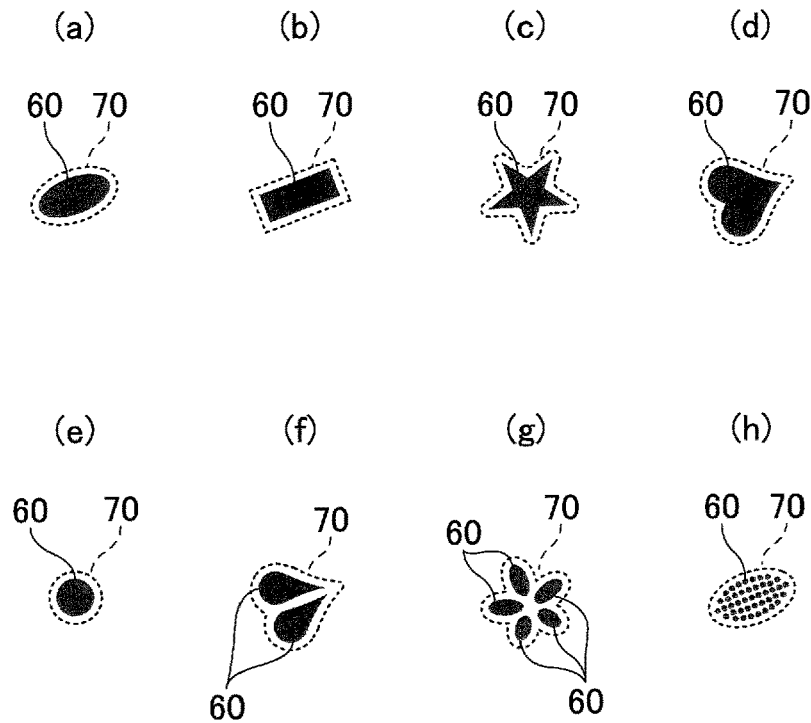
FIG. 4 shows schematic enlarged views of rigid portions and rigid areas according to embodiments of the present invention.

In FIG. 4, (a) to (e) illustrate examples in which one rigid portion 60 is included in one rigid area 70. Specifically, in each of these examples, one rigid portion 60 in the shape of (a) an ellipse, (b) a rectangle, (c) a star shape, (d) a heart shape, or (e) a circle is included in one rigid area 70.

On the other hand, as illustrated in (f) to (h) of FIG. 4, one rigid area 70 may include a plurality of rigid portions 60. In this case, the shapes and/or sizes of the rigid portions 60 included in the rigid area 70 may be the same or different from each other. In the examples illustrated in (f) to (h) of FIG. 4, a plurality of rigid portions 60 are arranged close to each other, and one motif is formed by the aggregate of the plurality of rigid portions 60.

For example, in FIG. 4(f), a broken heart motif is formed by arranging two raindrop-shaped rigid portions 60, and the rigid area 70 is arranged into a heart shape. Further, in FIG. 4(g), a flower-shaped motif is formed by an aggregate of a plurality of raindrop-shaped or elliptical rigid portions 60 that are radially arranged, and a rigid area 70 having such a flower shape is formed. Such a flower-shaped motif has high design quality and excellent aesthetic properties. Further, in FIG. 4(h), the rigid portions 60 are small embossed dots, and an elliptical motif is formed by an aggregate such small embossed dots to form an elliptical rigid area 70.

Note that the illustrated shapes of the rigid area 70 are merely examples. As described above, the shape of the rigid area 70 may differ depending on the number, shape, size, positional relationship, and the like of the rigid portions 60 included therein. Example shapes of the rigid area 70, in planar view, include but are not limited to a triangle; a quadrangle such as a trapezoid, a rhombus, and the like; other polygons; a circle; an elliptical shape; an almond shape; a raindrop shape; a star shape; a heart shape; a diamond shape; a spaded shape; a club shape; and the like.

The total area of the rigid portion 60 of the rigid area 70 is preferably greater than or equal to 2 mm$^2$ and less than or equal to 45 mm$^2$, and more preferably greater than or equal to 5 mm$^2$ and less than or equal to 29 mm$^2$. By arranging the total area to be within the above range, the rigidity of the hip hold portion H may be improved to prevent the formation of wrinkles in the recess, and at the same time, softness of the hip hold portion H may be ensured. In this way, the absorbent article 1 may provide good fit and excellent wearing comfort.

Note that in the case where a recess other than the first recess 51 is provided in the side region 10, for example, as illustrated in FIGS. 1 to 3, rigid areas 70 including one or more rigid portions 60 may also be arranged at corresponding positions of a second recess 52 that is arranged behind and adjacent to the first protrusion 41. In this case, by arranging the rigid areas 70 along an imaginary line passing through a bottom point of the second recess 52 and the center of the circle of curvature thereof, the formation of wrinkles in the second recess 52 may be prevented, and even when wrinkles are formed, the wrinkles may be dispersed, so that the sense of discomfort when the wrinkles come into contact with the skin may be reduced.

Also, in the case where the rigid areas 70 are provided at the corresponding positions of the first recess 51 and the second recess 52, the rigidity of the regions near the base ends of the first protrusion 41 arranged between the two recesses may be enhanced. Thus, curling and warping at the first protrusion 41 may be prevented and the peripheral edge portion of the hip hold portion H may be prevented from curling upward, for example.

Figure 5:
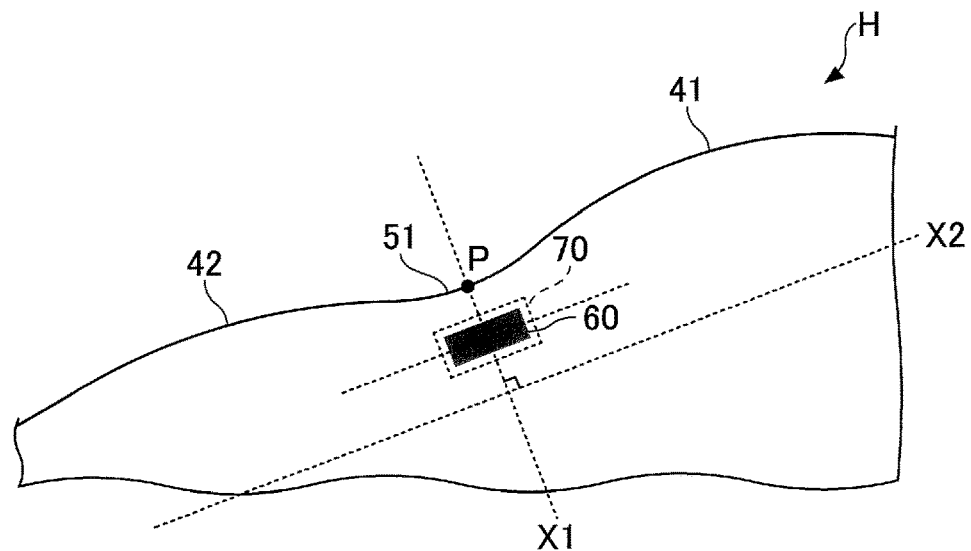
FIG. 5 shows a schematic partial enlarged view of a hip hold portion for illustrating an arrangement of a rigid portion and a rigid area according to an embodiment of the present invention.

In the case where the rigid portion 60 has an elongated shape, its longitudinal direction is preferably arranged to be substantially parallel to a second imaginary line X2 that is orthogonal to the above-mentioned first imaginary line X1 as shown in FIG. 5. Note that "substantially parallel to the second imaginary line X2" does not mean strictly parallel to the second imaginary line X2 but may mean, for example, within about ±15°, and more preferably within about ±5° with respect to the second imaginary line X2. Further, "elongated shape" may include a rectangular shape as shown in FIG. 5, an ellipse shape, a raindrop shape, an isosceles triangle with a base side that is shorter than the other two sides, and any other shapes with a length in one direction longer than a length in another direction. By arranging the longitudinal direction of the elongated rigid portion 60 to be substantially parallel to the second imaginary line X2 as described above, the area with enhanced rigidity may be extended in the direction of the second imaginary line X2, namely, in the direction orthogonal to the direction in which wrinkles are easily formed. As a result, the wrinkle preventing effect of the rigid portion 60 according to the present embodiment may be further enhanced.

Figure 6:
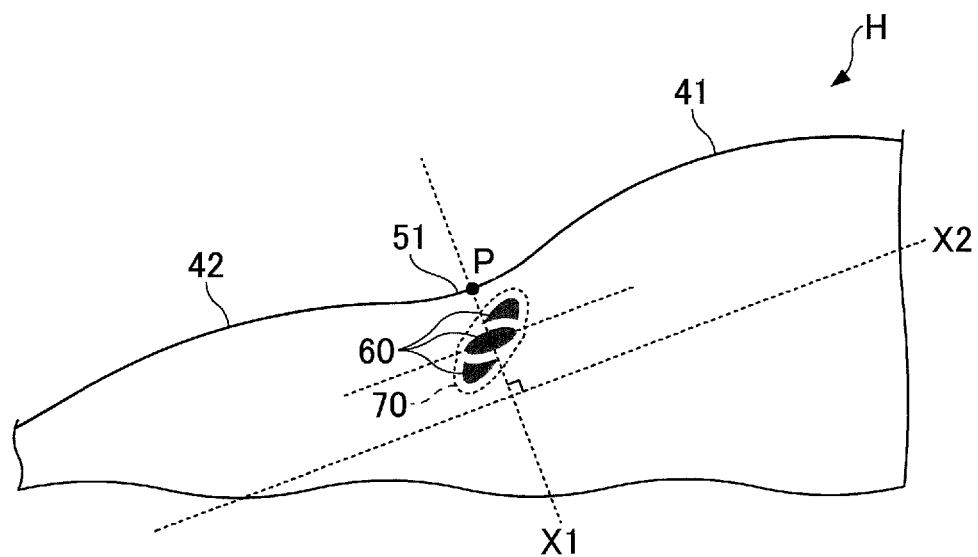
FIG. 6 shows schematic partial enlarged views of hip hold portions for illustrating other arrangements of a rigid portion and a rigid area according to embodiments of the present invention.
Figure 6:
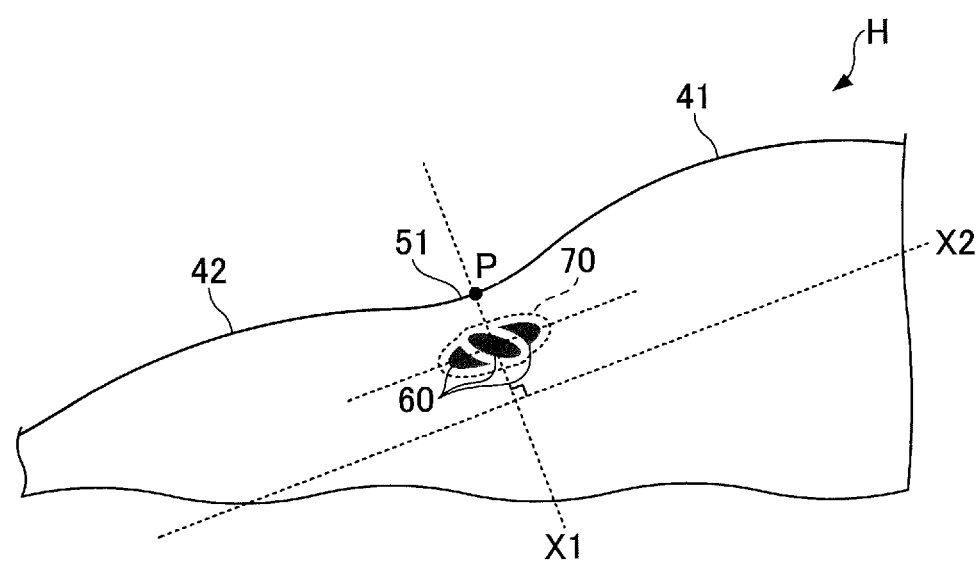
Figure 7:
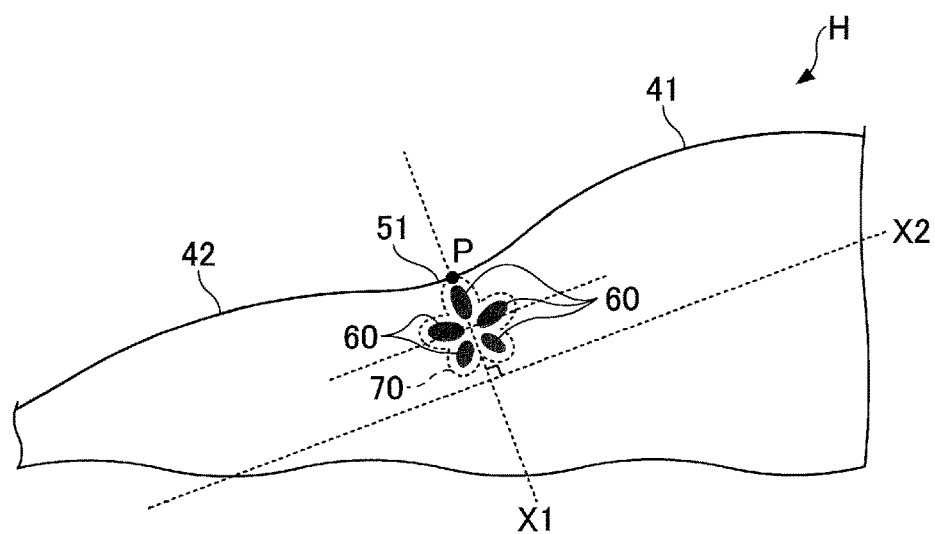
FIG. 7 shows schematic partial enlarged views of hip hold portions for illustrating other arrangements of a rigid portion and a rigid area according to embodiments of the present invention.
Figure 7:
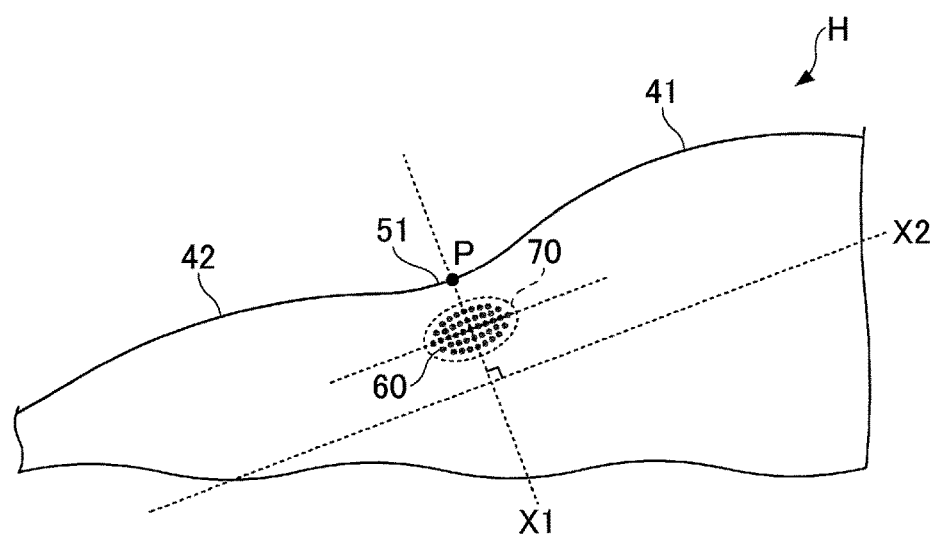
Figure 7:
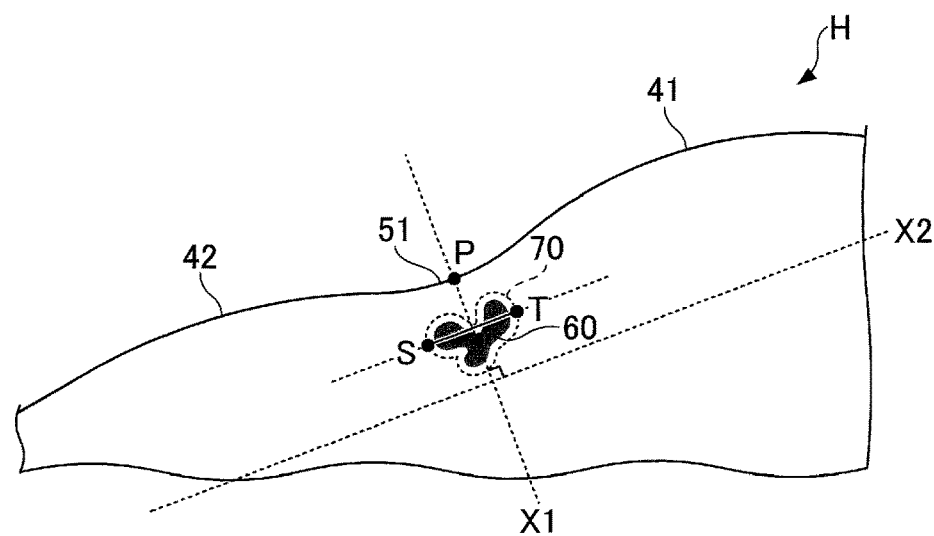

Also, in the case where the rigid area 70 has an elongated shape as a whole, the longitudinal direction of the elongated rigid area 70 is preferably arranged to be substantially parallel to the imaginary line X2 that is orthogonal to the above-described first imaginary line X1 as illustrated in FIG. 6(*b*) and FIG. 7(*a*) and FIG. 7(*b*). Note that "substantially parallel to the second imaginary line X2" does not mean strictly parallel to the second imaginary line X2 but may mean, for example, within about ±15°, and more preferably within about ±5° with respect to the second imaginary line X2. Further, the elongated shape of the rigid area 70 may include a rectangular shape, an ellipse shape, a raindrop shape, an isosceles triangle with a base side that is shorter than the other two sides, and any other shapes with a length in one direction longer than a length in another direction. By arranging the longitudinal direction of the elongated rigid area 70 to be substantially parallel to the second imaginary line X2 as described above, the area with enhanced rigidity may be extended in the direction of the second imaginary line X2, namely, in the direction orthogonal to the direction in which wrinkles are easily formed. In this way, the formation of wrinkles may be prevented across a wider range, and even when wrinkles are formed, the wrinkles may be effectively dispersed.

Note that the wrinkle preventing effect and the wrinkle dispersing effect can be enhanced as long as one of the above conditions relating to the rigid portion 60 and the rigid area 70 is satisfied. For example, FIG. 6(*a*) and FIG. 6(*b*) show rigid areas 70 including rigid portions 60 of similar shapes and sizes arranged in a similar manner. That is, only the orientations of the rigid areas 70 of (a) and (b) in FIG. 6 differ from each other. In the example of FIG. 6(*a*), the longitudinal direction of the central elliptical rigid portion 60 among the three rigid portions 60 is arranged substantially parallel to the above-mentioned second imaginary line X2. On the other hand, in the example of FIG. 6(*b*), the longitudinal direction of the elliptical rigid area 70 is arranged substantially parallel to the above-mentioned second imaginary line X2. Although the overall orientations of the rigid areas 70 in the examples of FIG. 6(*a*) and FIG. 6(*b*) differ from each other, both of these examples satisfy at least one of the above-described arrangement direction conditions relating to the rigid portion 60 and the rigid area 70, and as such, the above-described effects may be achieved in both of these examples.

However, the example as shown in FIG. 6(*b*) in which the longitudinal direction of the elongated shape of the rigid area 70 is arranged to be substantially parallel to the second imaginary line X2 may be preferable, and more preferably, both of the rigid portion 60 and the rigid area 70 are arranged into shapes that satisfy the above conditions.

Note that the rigid area 70 and the rigid portion 60 may be assumed to have elongated shapes if at least two line segments with differing lengths can be obtained upon drawing at least two line segments connecting two points on the outline defining, the shape of the rigid portion 60 or the rigid area 70. For example, when the rigid portion 60 and the rigid area 70 have shapes as shown in FIG. 7(*c*), the direction of the longest line segment ST among the line segments obtained by connecting two points on the outline defining the shape of the rigid area 70 is preferably arranged to be substantially parallel to the second imaginary line X2, and in this way, the area with enhanced rigidity may be extended more widely in the direction of the second imaginary line X2. In this way, the formation of wrinkles in the vicinity of a recess where stress is likely to concentrate may be more effectively prevented. Also, even when wrinkles are formed, the effect of dispersing wrinkles may be further enhanced.

The number of the rigid areas 70 arranged on the first imaginary line X1 may be one or more. In the case of arranging a plurality of rigid areas 70, their shapes and/or sizes may be the same or different from each other.

Figure 8:
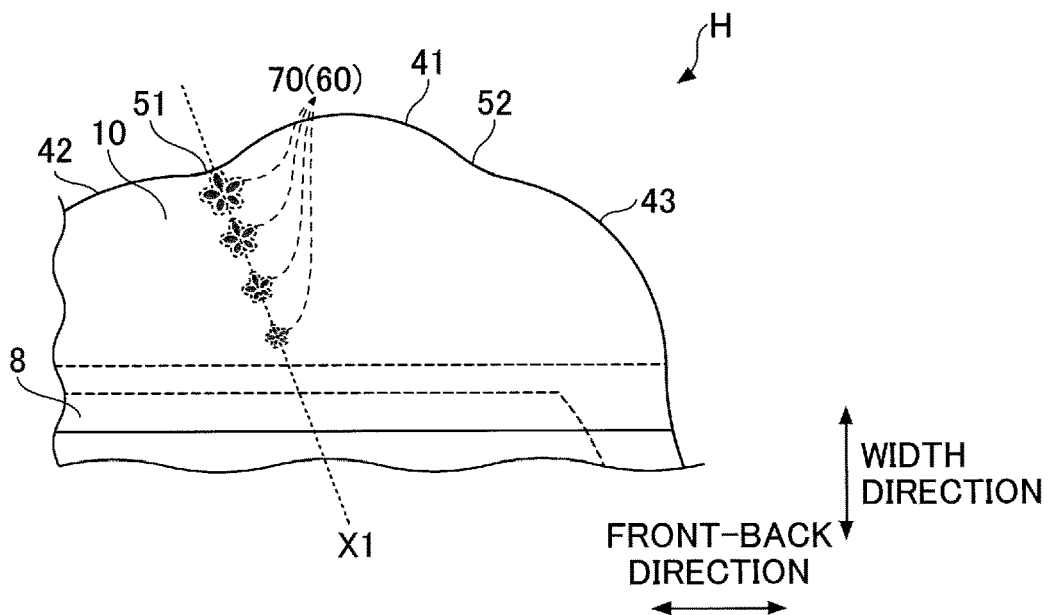
FIG. 8 shows a partial enlarged view of a hip hold portion according to an embodiment of the present invention.

In the case of arranging a plurality of rigid areas 70 along the first imaginary line X1, the size of the rigid area 70 arranged at the outer side is preferably maximized, and the size of the rigid area 70 at the inner side is preferably arranged to be smaller than the rigid area 70 at the outer side. That is, the area of a rigid area 70 (or the area of a rigid portion 60 within the rigid area 70) arranged at a position closer to the front-back direction centerline CL is arranged to be smaller than the area of a rigid area 70 (or the area of a rigid portion 60 within the rigid area 70) arranged at a position farther away from the centerline CL. As shown in FIG. 8, when arranging three or more rigid areas 70, the size of the rigid areas 70 is preferably gradually reduced from the outer side toward the inner side. In this case, the rigid areas 70 having different areas are preferably arranged to have similar shapes. Specifically, the shapes of the rigid areas 70 themselves and the shapes and arrangement of the rigid portions 60 included in the rigid areas 70 are preferably arranged to be similar.

By arranging the rigid area 70 toward the peripheral edge of the recess to be larger and arranging the rigid area 70 farther away from the peripheral edge (toward the inner side) to be smaller, the wrinkle preventing effect and the wrinkle dispersing effect may be maintained at the peripheral edge of the recess where stress is likely to concentrate, and at the same time, discomfort that may be caused by the rigid portion 60 may be reduced at the inner side portion that is more likely to come into contact with the skin.

Although the position on the imaginary line X1 at which the rigid areas 70 is arranged is not particularly limited, for example, as shown in FIGS. 3 and 8, the arrangement position in the width direction may reach inward up to the boundary with the absorbent article main body 8. Also, the rigid area 70 may be arranged to be in contact with the outline of the hip-hold portion H.

Figure 9:
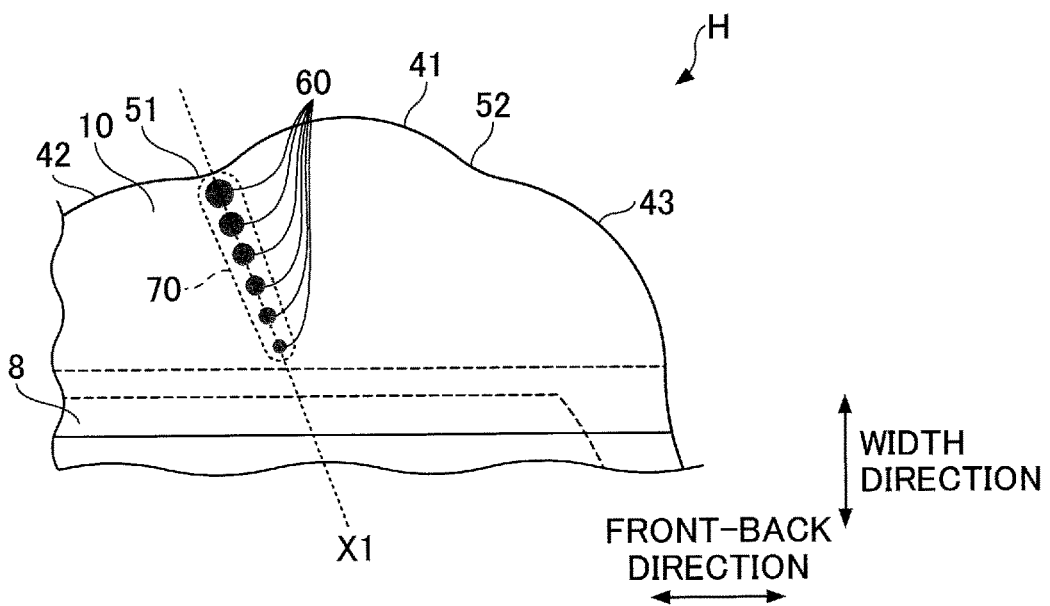
FIG. 9 shows a partial enlarged view of a hip hold portion according to an embodiment of the present invention.

For example, as shown in FIG. 9, a plurality of adjacent rigid portions 60 may be continuously arranged along the first imaginary line X1 to form a strip-shaped rigid area 70 reaching up to the main body 8.

Also, as shown in FIG. 1, a plurality of embossed dots DE may be arranged along a peripheral edge portion of the side region 10 of the hip hold portion H, for example. The embossed dots DE form an aggregation of small dotted compressed portions that may be formed by an embossing process such as a hot embossing process or an ultrasonic embossing process, for example. The embossed dots DE are provided mainly for the purpose of bonding the layered structure of the side nonwoven fabric 7 and the backsheet 2 at the peripheral edge portion of the absorbent article and enhancing the rigidity at such portion.

Although the shape of the embossed dot DE is circular in the example shown in FIG. 1 and the like, the shape of the embossed dot DE may also be in other shapes including a triangle; quadrangles such as a trapezoid, a tetragon, a rhombus, and the like; other polygons; an ellipse; a raindrop shape; a star shape; a heart shape; and the like. The area of each embossed dot DE is preferably greater than or equal to 0.2 mm$^2$ and less than or equal to 1.8 mm$^2$, and more preferably greater than or equal to 0.5 mm$^2$ and less than or equal to 0.8 mm$^2$. By arranging the area of the embossed dot DE to be within the above range, the peripheral edge of the absorbent article 1 may be adequately joined and appropriate rigidity may be provided.

In the case of providing the embossed dots DE along the peripheral edge portion, the area of the rigid portion 60 in the rigid area 70 is preferably arranged to be greater than or equal to 10 times and less than or equal to 25 times the area of one embossed dot DE. Note that in the case where a plurality of rigid portions 60 are included in one rigid area 70, the total area of the rigid portions 60 included in one rigid area 70 may be arranged to be within the above range. By arranging the area of the rigid portion 60 included in the rigid area 70 to be within the above range, well-balanced moderate rigidity may be achieved in the peripheral region of the hip hold portion H and the inner region thereof.

Note that the rigid area 70 may additionally be provided at a position other than the position on the first imaginary line X1 depending on the shapes and/or sizes of the protrusions and recesses arranged at the side region 10.

Also, the rigid area 70 may be provided in a region other than the side region 10 of the hip hold portion H. For example, the rigid area 70 may be provided in a back region 20 of the hip hold portion H where the topsheet 3 and the backsheet 2 are laminated. In the case where the outline of the back region 20 is uneven and includes a recess, for example, one or more rigid areas 70 may be provided on an imaginary line passing through a bottom point of the recess of the back region 20 and a center of a circle of curvature of the curve at the bottom point. In this way, formation of wrinkles at the back region 20 may also be prevented.

Note that the position of the first protrusion 41 having the greatest width in the front-back direction may be further backward with respect to a middle position of the hip hold portion H in the front-back direction. Because backward regions of the hip hold portion H are more prone to movement in the width direction, stress tends to gather easily in the first recess 51, which is in front of and adjacent to the first protrusion 41. However, even in such a case, by arranging a rigid area 70 including one or more rigid portions 60 with enhanced rigidity on the imaginary line X1, formation of wrinkles in the first recess 51 can be effectively prevented.

The present application is based on and claims priority to Japanese Patent Application No. 2016-165033 filed on Aug. 25, 2016, the entire contents of which are incorporated herein by reference.

DESCRIPTION OF THE REFERENCE NUMERALS 1 absorbent article
2 backsheet
3 topsheet
4 absorbent member
5 wrapping sheet
7 side nonwoven fabric
8 main body (absorbent article main body)
10 side region
20 back region
41 first protrusion
42 second protrusion
51 first recess
52 second recess
60 rigid portion
70 rigid area
H hip hold portion
W wing portion DE embossed dot
WG wing
CL front-back direction centerline
X1 first imaginary line (straight line passing through bottom point of first recess and center of circle of curvature)
X2 second imaginary line (straight line orthogonal to first imaginary line)

The invention claimed is:

1. An absorbent article comprising:
a main body including a liquid-pervious topsheet, a liquid-impervious backsheet, and an adsorbent member arranged between the topsheet and the backsheet; and
a hip hold portion;
wherein the main body has a shape with a prescribed length in a front-back direction and a prescribed width in a direction orthogonal to the front-back direction;
wherein the hip hold portion includes a side region protruding from a backward side portion of the main body, the side region including a first protrusion including a portion with a greatest width from a front-back direction centerline, a first recess that is in front of and adjacent to the first protrusion, and a second protrusion that is in front of and adjacent to the first recess; and
wherein an outline of the first recess includes a curved line, and a rigid area including one or more rigid portions with enhanced rigidity is provided on a first imaginary line passing through a bottom point of the first recess and a center of a circle of curvature of a curve at the bottom point of the first recess,
wherein a plurality of embossed dots are provided at a peripheral portion of the side region, and an area of the rigid portion in the rigid area is greater than or equal to 10 times and less than or equal to 25 times an area of one of the embossed dots.

2. The absorbent article according to claim 1, wherein the rigid portion or the rigid area has an elongated shape, and a longitudinal direction of the elongated shape is substantially parallel to a second imaginary line that is orthogonal to the first imaginary line.

3. The absorbent article according to claim 1, wherein the rigid portion is an embossed portion.

4. The absorbent article according to claim 1, wherein a plurality of the rigid portions are radially arranged in the rigid area to form a flower shape.

5. An absorbent article comprising:
a main body including a liquid-pervious topsheet, a liquid-impervious backsheet, and an adsorbent member arranged between the topsheet and the backsheet; and
a hip hold portion;
wherein the main body has a shape with a prescribed length in a front-back direction and a prescribed width in a direction orthogonal to the front-back direction;
wherein the hip hold portion includes a side region protruding from a backward side portion of the main body, the side region including a first protrusion including a portion with a greatest width from a front-back direction centerline, a first recess that is in front of and adjacent to the first protrusion, and a second protrusion that is in front of and adjacent to the first recess; and
wherein an outline of the first recess includes a curved line, and a rigid area including one or more rigid portions with enhanced rigidity is provided on a first imaginary line passing through a bottom point of the first recess and a center of a circle of curvature of a curve at the bottom point of the first recess,
wherein a plurality of the rigid areas are arranged along the first imaginary line, and an area of a rigid area closer to the centerline is arranged to be smaller than an area of a rigid area farther away from the centerline.

* * * * *